United States Patent
Miller

(10) Patent No.: US 11,744,498 B2
(45) Date of Patent: Sep. 5, 2023

(54) CATHETER SYSTEM

(71) Applicant: Covidien LP, Mansfield, MA (US)

(72) Inventor: David J. Miller, Boulder, CO (US)

(73) Assignee: Covidien LP, Mansfield, MA (US)

( * ) Notice: Subject to any disclaimer, the term of this patent is extended or adjusted under 35 U.S.C. 154(b) by 375 days.

(21) Appl. No.: 16/932,212

(22) Filed: Jul. 17, 2020

(65) Prior Publication Data

US 2022/0015676 A1 Jan. 20, 2022

(51) Int. Cl.
| | |
|---|---|
| *A61B 5/20* | (2006.01) |
| *A61B 5/145* | (2006.01) |
| *A61B 5/1459* | (2006.01) |
| *A61B 5/00* | (2006.01) |
| *A61M 25/04* | (2006.01) |
| *A61M 25/00* | (2006.01) |

(52) U.S. Cl.
CPC ............ *A61B 5/201* (2013.01); *A61B 5/1459* (2013.01); *A61B 5/14546* (2013.01); *A61B 5/208* (2013.01); *A61B 5/6852* (2013.01); *A61B 5/7275* (2013.01); *A61M 25/04* (2013.01); *A61M 25/0017* (2013.01); *A61M 2205/3576* (2013.01); *A61M 2205/52* (2013.01)

(58) Field of Classification Search
CPC ....... A61B 5/1455; A61B 5/201; A61B 5/208; A61B 5/1459; A61B 5/14546; A61B 5/6852
See application file for complete search history.

(56) References Cited

U.S. PATENT DOCUMENTS

| | | | |
|---|---|---|---|
| 4,448,207 | A | 5/1984 | Parrish |
| 5,389,217 | A | 2/1995 | Singer |
| 5,463,906 | A | 11/1995 | Spani et al. |
| 5,916,153 | A | 6/1999 | Rhea, Jr. et al. |
| 6,053,873 | A | 4/2000 | Govari et al. |
| 8,715,254 | B2 | 5/2014 | Nishtala |
| 8,827,924 | B2 | 9/2014 | Paz et al. |
| 9,655,555 | B2 | 5/2017 | Burnett et al. |
| 9,662,058 | B2 | 5/2017 | Burnett et al. |

(Continued)

FOREIGN PATENT DOCUMENTS

| | | |
|---|---|---|
| WO | 2004/100788 A1 | 11/2004 |
| WO | 2012/176194 A1 | 12/2012 |

(Continued)

OTHER PUBLICATIONS

International Search Report and Written Opinion of International Application No. PCT/US2021/041458, dated Oct. 29, 2021, 16 pp.

(Continued)

*Primary Examiner* — Marjan Fardanesh
(74) *Attorney, Agent, or Firm* — Shumaker & Sieffert, P.A.

(57) ABSTRACT

In one example, the disclosure relates to a catheter system comprising an elongated body defining a lumen. The elongated body comprising a proximal portion and a distal portion. An anchoring member is positioned on the proximal portion of the elongated body. The anchoring member configured to anchor the proximal portion of the elongated body to a patient. The catheter system includes one or more sensors positioned on the elongated body. The one or more sensors are configured to sense a parameter of a fluid within the lumen of the elongated body. The catheter system includes memory positioned on the elongated body, the memory configured to store patient-specific information.

18 Claims, 7 Drawing Sheets

(56) References Cited

U.S. PATENT DOCUMENTS

| | | |
|---|---|---|
| 9,857,210 B2 | 1/2018 | Mantinband et al. |
| 10,307,564 B2 | 6/2019 | Erbey, II et al. |
| 10,433,790 B2 | 10/2019 | Ofek et al. |
| 10,506,965 B2 | 12/2019 | Cooper et al. |
| 10,524,694 B2 | 1/2020 | Hunter |
| 10,542,923 B2 | 1/2020 | Chang et al. |
| 2004/0215067 A1 | 10/2004 | Stiger et al. |
| 2006/0100743 A1 | 5/2006 | Townsend et al. |
| 2009/0043184 A1 | 2/2009 | Fjield et al. |
| 2009/0105799 A1 | 4/2009 | Hekmat et al. |
| 2009/0143673 A1 | 6/2009 | Drost et al. |
| 2009/0285761 A1 | 11/2009 | Wang et al. |
| 2010/0204765 A1 | 8/2010 | Hall et al. |
| 2011/0046514 A1 | 2/2011 | Greenwald et al. |
| 2011/0208013 A1 | 8/2011 | Phan et al. |
| 2013/0237901 A1 | 9/2013 | Woo |
| 2015/0366462 A1 | 12/2015 | Ramos et al. |
| 2016/0183819 A1 | 6/2016 | Burnett et al. |
| 2016/0258798 A1 | 9/2016 | Muhammad et al. |
| 2016/0310711 A1 | 10/2016 | Luxon et al. |
| 2017/0035342 A1 | 2/2017 | Elia et al. |
| 2017/0079571 A1 | 3/2017 | Washington |
| 2017/0113000 A1 | 4/2017 | Tobescu et al. |
| 2017/0348512 A1 | 12/2017 | Or et al. |
| 2017/0367636 A1 | 12/2017 | Mantinband et al. |
| 2018/0110455 A1 | 4/2018 | Chang et al. |
| 2018/0188097 A1 | 7/2018 | Levine |
| 2019/0069831 A1 | 3/2019 | Kuck et al. |
| 2019/0150801 A1 | 5/2019 | Suehara et al. |
| 2019/0343445 A1 | 11/2019 | Burnett et al. |
| 2019/0358387 A1 | 11/2019 | Elbadry et al. |
| 2020/0022636 A1 | 1/2020 | Suehara et al. |
| 2020/0022638 A1 | 1/2020 | Suehara et al. |
| 2020/0085378 A1 | 3/2020 | Burnett et al. |

FOREIGN PATENT DOCUMENTS

| | | |
|---|---|---|
| WO | 2014/043650 A2 | 3/2014 |
| WO | 2019/140224 A2 | 7/2019 |
| WO | 2020/033752 A1 | 2/2020 |

OTHER PUBLICATIONS

"Flow measurement", Wikipedia, the Free Encyclopedia, last edited on Jan. 2, 2020, accessed on Jul. 28, 2020, 17 pp.

U.S. Appl. No. 16/858,321, filed Apr. 24, 2020, naming inventor Miller.

U.S. Appl. No. 16/858,252, filed Apr. 24, 2020, naming inventor Miller.

U.S. Appl. No. 16/858,209, filed Apr. 24, 2020, naming inventor Miller.

U.S. Appl. No. 16/858,233, filed Apr. 24, 2020, naming inventor Miller.

U.S. Appl. No. 16/858,287, filed Apr. 24, 2020, naming inventor Miller.

International Preliminary Report on Patentability from International Application No. PCT/US2021/041458 dated Jan. 26, 2023, 12 pp.

Office Action from U.S. Appl. No. 16/858,252 dated Jan. 5, 2023, 16 pp.

Final Office Action from U.S. Appl. No. 16/858,252 dated May 22, 2023, 17 pp.

Response to Office Action dated Jan. 5, 2023 from U.S. Appl. No. 16/858,252, filed Apr. 3, 2023, 11 pp.

US 11,744,498 B2

CATHETER SYSTEM

TECHNICAL FIELD

This disclosure relates to medical devices, more particularly, to catheters.

BACKGROUND

Medical devices, such as catheters, may be used to assist a patient in voiding their bladder. In some instances, such catheters may be used before, during, and/or after surgery. In the case of using a catheter to assist a patient in voiding their bladder, a Foley catheter is a type of catheter used for longer time periods than a non-Foley catheter. Some Foley catheters are constructed of silicon rubber and include an anchoring member, that may be an inflatable balloon inflated in a patient's bladder to serve as an anchor, so a proximal end of the catheter does not slip out of the patient's bladder.

SUMMARY

The disclosure describes catheters (e.g., a Foley catheter) and techniques for making and using such catheters. A catheter system may include memory configured to store patient-specific data, e.g., sensor information and/or other information that is specific to the patient in which the catheter is employed. The sensor information may include one or more sensed parameters of a fluid within a lumen of the catheter, e.g., where the one or more sensed parameters is sensed by one or more sensors positioned on the catheter. The memory may be configured to store the patient-specific data from one or more external devices configured to be operatively coupled to the catheter. The patient-specific data may include a history of patient-specific data. The patient-specific data may be stored on the memory located on the catheter and the history of patient-specific data may be accessed by the one or more external devices. The patient-specific data, including the history of patient-specific data may be retained on the memory as long as the catheter is used with a patient.

The memory may store patient-specific data used by processing circuitry to generate an acute kidney injury (AKI) risk score that may be updated (e.g., substantially continuously or periodically) and accessed by one or more external devices separate from the catheter. The processing circuitry may be part of the catheter or part of an external device. Regardless of processor that generates the AKI risk score, the AKI risk score may be stored on the memory so the AKI risk score may be accessed later (e.g., for clinician review and/or updating based on new patient information). Additionally, or alternatively, the memory may store an AKI risk score generated by another external device. For example, patient specific information stored on the memory may be accessed by an external device upon a patient moving from a first location (e.g., an operating room) to a second location (e.g., a post-operation room). The external device in the second location may then access the AKI risk score and/or the patient-specific data stored in the memory. The patient-specific data in the memory may also be accessed by the one or more external devices, including the second external device, to calculate a risk of AKI score. The AKI risk score may be calculated continuously and in real time and in other examples the AKI risk score may be calculated periodically and non-real time. The patient-specific data used to calculate the AKI score may include pre-operative patient data, intraoperative patient data and post-operative data that is updated as new patient-specific data is generated.

In one example, the disclosure relates to a catheter system includes an elongated body defining a lumen. The elongated body includes a proximal portion and a distal portion. An anchoring member is positioned on the proximal portion of the elongated body. The anchoring member configured to anchor the proximal portion of the elongated body to a patient. The catheter system includes one or more sensors positioned on the elongated body. The one or more sensors are configured to sense a parameter of a fluid within the lumen of the elongated body. The catheter system includes memory positioned on the elongated body, the memory configured to store patient-specific information.

In another example, the disclosure relates to a method that includes sensing, with one or more sensors positioned on a distal portion of an elongated body anchored to a patient with an anchoring member positioned on a proximal portion of the elongated body, a parameter of a fluid within a lumen defined by the elongated body. The method includes storing, with a memory positioned on the distal portion of the elongated body, patient-specific information that includes sensor information collected by the at least one sensor.

In another example, the disclosure relates to a catheter system includes an elongated body defining a lumen. The elongated body includes a proximal portion and a distal portion. An anchoring member is positioned on the proximal portion of the elongated body. The anchoring member is configured to anchor the proximal portion of the elongated body to a patient. The catheter system includes one or more sensors positioned on the elongated body. The one or more sensors are configured to sense a parameter of a fluid within the lumen of the elongated body. The catheter system includes memory positioned on the distal portion of the elongated body. The memory configured to store patient-specific information, wherein the patient-specific information includes sensor information collected by the one or more sensors and patient-data collected from one or more external devices configured to be coupled to the catheter system.

The details of one or more examples are set forth in the accompanying drawings and the description below. Other features, objects, and advantages will be apparent from the description and drawings, and from the claims.

DETAILED DESCRIPTION

Figure 1:
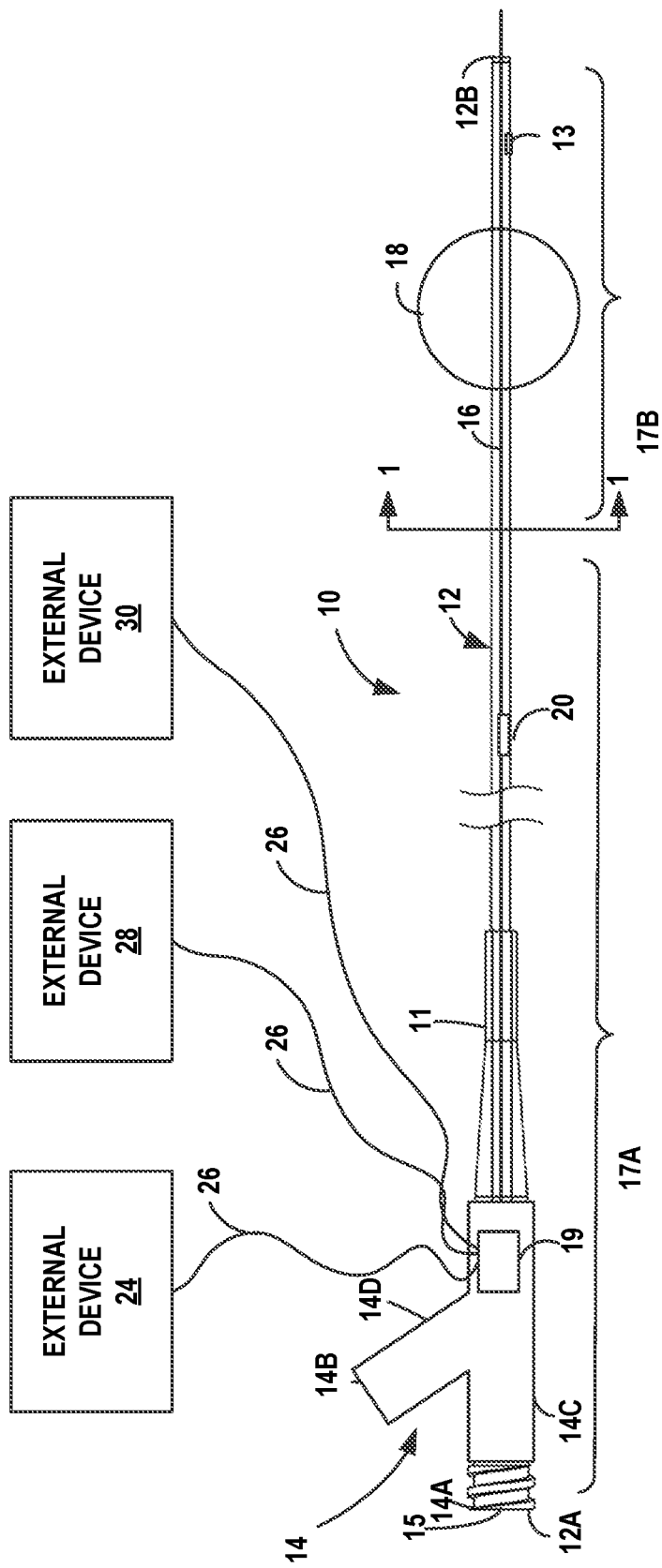
FIG. 1 is a conceptual diagram illustrating an example medical device system including an example catheter in accordance with an example of the disclosure.

In general, the disclosure describes medical devices and systems including a catheter, such as a Foley catheter or other urinary or non-urinary catheter, and methods of using the same. As will be described below, examples of the disclosure may include catheters having one or more memories physically coupled to the catheter (e.g., attached to the elongated body of the catheter), where the memory may be configured to store patient-specific information such as pre-operative, intraoperative, and/or post-operative patient specific information. The patient-specific information may include sensor information generated by one or more sensors of the catheter, e.g., from a sensor on the elongated body that is configured to sense one or more parameters of a fluid, such as urine, within a lumen of the catheter body (e.g., the drainage lumen). Additionally, or alternatively, the patient specific information may include information inputted by a clinician or other user for storage on the catheter memory and/or information generated by one or more external devices separate from the catheter that is transferred to the catheter memory for storage. Examples of patient-specific information that may be stored on the memory may include the start and stop of different procedural epochs for the patient, information related to drug(s) administered to the patient, blood transfusions that the patient has received, aortic cross-clamping times for the patient, other intraoperative events, one or more sensed parameters of a patient, such as heart rate, by sensors coupled to an external device, and/or electronic medical records of the patient. In some examples, the catheter memory may store may information regarding patient lab results such as hematocrit, arterial partial pressure of oxygen, AKI biomarker tests, serum creatinine, or other lab results for labs performed on the patient, e.g., during the course of patient treatment. In some examples, the information stored on the catheter memory may be manually completed by the clinician or be automatically added, e.g., from an electronic medical record.

The patient-specific information stored on the catheter memory may include sensor information related to fluid (e.g., urine) within a lumen of the catheter, e.g., that is sensed by one or more sensors on the catheter. In some examples, sensed parameters of the fluid may include flow rate of the fluid, temperature of the fluid, density of the fluid, and/or oxygen content of the fluid. In some examples, the sensed parameters may be used to monitor urine output/rate of urine production of a patient and/or the amount of oxygen dissolved in the urine. Such information may be useful in monitoring the renal function of the patient, e.g., while the catheter is inserted within the patient.

As will be described below, the patient-specific information may be stored on the catheter memory so that the information travels with the patient through the course of the patient's operative care, e.g., while the catheter is within the patient. The patient-specific information may be accessed at one or more points during the process of caring for the patient, e.g., to allow one or more clinician to review the information. In some examples, the patient specific information stored on the catheter memory may be accessed by processing circuitry of the catheter and/or one or more external devices to generate an AKI risk score for a patient based at least in part on the stored information.

For ease of description, examples of the disclosure are primarily described with regard to a catheter such as a Foley catheter being employed as a urinary catheter within a patient. For example, in some instances, the present disclosure is directed to a Foley catheter including one or more memories configured to facilitate storage of patient-specific information that includes one or more physiological parameters and history of physiological parameters sensed by one or more sensors. However, examples of the present disclosure are not limited to Foley-type catheters or urinary catheters.

Acute kidney injury (AKI) is a complication that occurs commonly after major surgeries such as cardiac surgery and other operations that are long and involve significant blood loss or fluid shifts. The primary cause of surgery-associated AKI may be hypoxia of the kidneys. Renal hypoxia may cause degradation of renal function, that, after one to three days, may cause a reduced urine output and/or an accumulation of waste products in the bloodstream. This accumulation of fluid and waste products may delay the recovery of the patient leading to more extended and expensive hospital stays and sometimes requiring renal replacement therapy.

One approach to preventing AKI is to monitor the oxygenation status of a patient's kidneys. However, accurate monitoring may be challenging due to the inaccessibility of the kidneys that are deep in the abdominal cavity. Near-Infrared spectroscopy (NIRS) may measure regional oximetry and may have some utility in infants and slender adults but does not have the depth of penetration and specificity required for most adults.

Systemic vital signs like cardiac output, blood pressure, and hematocrit may be useful but may not always be sufficient to properly monitor the kidneys. When the body becomes stressed, such as during cardiac surgery, blood flow may be reduced to vital organs in a reliable sequence based on the criticality of the organs. It has been observed that the skin may be the first to realize reduced blood flow, followed by the intestines and then the kidneys, then the brain and then the heart. The skin and the intestines may withstand short hypoxic episodes and recover normal function, but the kidneys may be damaged with even brief hypoxic episodes.

Examples of the present disclosure may be related to device features to aid in the monitoring of the kidneys of a patient. In some examples, the approach is to store patient-specific data, such as a patient's history of sensor information and inputted data, onboard a catheter. Such a device may allow clinicians to know a patient's history as the patient is moved from one area of care to another. In some examples, a catheter may be used on one monitor for a procedure and then connected to another monitor for patient recovery and the data obtained during the medical procedure may be downloaded to the recovery room monitor. In some examples sensor information may be recorded completely or partially on a memory located on or within the catheter, such that when the catheter is connected to a new monitor the new monitor may display historic data from the prior monitor or monitors and in doing so allow a clinician to see a patient's historic data.

In some examples, monitoring information recorded during surgery by a memory on, coupled to or formed with a catheter such as a Foley Catheter may be used to calculate a risk of AKI score. The risk of AKI score may be based on pre-operative patient characteristics and updated (e.g., substantially continuously or periodically) as new patient-specific information or data is inputted or generated. In some examples, the AKI risk score may be summarized in a procedural report that includes the AKI risk score and other information like length or intensity of hypoxia. The summary report may be recorded to a memory on the catheter and accessed on other devices, added to the electronic medical record and travel with the patient from one area to another.

In some examples, the information stored on a catheter memory may provide substantially continuous data to a real-time prediction algorithm that determines AKI risk. In some examples, the algorithm may be stored on memory on the catheter. The algorithm may calculate and display, via a monitor, a continuously updated patient risk of developing AKI. The algorithm may update AKI risk in real time based upon measurements made during a procedure. Such measurements may include cardiac output, blood pressure, pulse oximetry, hematocrit, arterial partial pressure of oxygen, AKI biomarker tests, serum creatinine, or any other lab results or sensed parameters. In some examples, the algorithm may account for events such as the start and stop of surgery epochs, drug administrations, blood transfusions, aortic cross-clamping, or other intraoperative events. In some examples, the continuously updated results of the real-time prediction algorithm may be stored on the memory on the catheter. When a patient is moved to a new location and coupled to a new monitor, a clinician or intensivist may then observe the results of the real-time AKI prediction algorithm when the patient left the last location. Further, any patient-specific information collected during the patient's move may be used to update the real-time AKI prediction algorithm and provide the clinician or intensivist with a real-time AKI patient status.

As noted above, a Foley catheter may be a type of urinary catheter used in the examples of the present disclosure. A Foley catheter may be modified in the manner described herein to facilitate the storage of inputs such as clinician pre-operative data and sensor measurements of urine parameters for renal monitoring. In some examples, one or more sensors may be used in conjunction with a Foley Catheter to monitor renal function. In some examples, the sensor(s) may provide data indicating detection of and prevention of acute kidney injury.

FIG. 1 is a conceptual side elevation view of an example medical device 10, that includes elongated body 12 including hub 14, and anchoring member 18. In some examples, medical device 10 is a catheter, such as a Foley catheter. While a Foley catheter and its intended use is primarily referred to herein to describe medical device 10, in other examples, medical device 10 may be used for other purposes, such as to drain wounds or for intravascular monitoring or medical procedures.

Elongated body 12 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., so proximal end 12B of elongated body 12 is within the patient's urethra and bladder, distal portion 17A may remain outside of the body of the patient.

As shown in FIG. 1, elongated body 12 may be a body extending from distal end 12A to proximal end 12B and that defines one or more inner lumens. In the example shown in FIGS. 1 and 2, elongated body 12 defines lumen 34 and lumen 36 (shown in FIG. 2). In some examples, lumen 34 may be a drainage lumen for draining a fluid from a target site, such as a bladder. In other examples lumen 34 may be used for any other suitable purpose, such as to deliver a substance or another medical device to a target site within a patient. Lumen 34 may extend from fluid opening 13 to fluid opening 14A. Both fluid opening 13 and fluid opening 14A may be fluidically coupled to lumen 34, so a fluid may flow from one of fluid opening 13 or fluid opening 14A to the other of fluid opening 13 or fluid opening 14A through lumen 34. In the example where lumen 34 is a drainage lumen, fluid opening 13 and fluid opening 14A may be drainage openings. In the example shown in FIG. 1, distal end 12A of elongated body 12 includes hub 14 and is mechanically connected to hub 14 via an adhesive, welding, or another suitable technique or combination of techniques.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal and proximal portions of elongated body 12 may each have any suitable length.

Hub 14 is at a distal end of elongated body 12 and defines an opening through which the one or more inner lumens (e.g., lumen 34 shown in FIG. 2) of elongated body 12 may be accessed and, in some examples, closed. While hub 14 is shown in FIG. 1 as having two arms, 14C and 14D, (e.g., a "Y-hub"), hub 14 may have any suitable number of arms, that may depend on the number of inner lumens defined by elongated body 12. For example, each arm may be fluidically coupled to a respective inner lumen of elongated body 12. In the example of FIG. 1, hub 14 comprises a fluid opening 14A, that is fluidically coupled to lumen 34, and an inflation opening 14B, that is fluidically coupled to an inflation lumen 36 (shown in FIG. 2) of elongated body 12. In examples in which anchoring member 18 does not include an expandable balloon, rather than defining inflation lumen 36, elongated body 12 may define an inner lumen configured to receive a deployment mechanism (e.g., a pull wire or a push wire) for deploying an expandable structure anchoring member 18 and hub 14 may comprise fluid opening 14A and an opening 14B via which a clinician may access the deployment mechanism.

In examples in which medical device 10 is a Foley catheter, a fluid collection container (e.g., a urine bag) may be attached to fluid opening 14A for collecting urine draining from the patient's bladder. Inflation opening 14B may be operable to connect to an inflation device to inflate anchoring member 18 positioned on proximal portion 17B of medical device 10. Anchoring member 18 may be uninflated or undeployed when not in use. Hub 14 may include connectors, such as connector 15, for connecting to other devices, such as the fluid collection container and the inflation source. In some examples, medical device 10 includes strain relief member 11, that may be a part of hub 14 or may be separate from hub 14.

Proximal portion 17B of medical device 10 comprises anchoring member 18 and fluid opening 13. Anchoring member 18 may include any suitable structure configured to expand from a relatively low profile state to an expanded state in that anchoring member 18 may engage with tissue of a patient (e.g., inside a bladder) to help secure and prevent movement of proximal portion 17B out of the body of the patient. For example, anchoring member 18 may include an anchor balloon or other expandable structure. When inflated or deployed, anchoring member 18 may function to anchor medical device 10 to the patient, for example, within the patient's bladder. In this manner, the portion of medical device 10 on the proximal side of anchoring member 18 may not slip out of the patient's bladder. Fluid opening 13 may be positioned on the surface of longitudinal axis of medical device 10 between anchoring member 18 and the proximal end 12B (as shown) or may be positioned at the proximal end 12B.

In accordance with examples of the disclosure, medical device 10 may include memory that may be configured to store patient-specific information, such as sensor information including one or more parameters of a fluid within lumen 34 (FIG. 2) of elongate body 12 and/or other patient-specific information such as that described herein. For example, memory 19 may be located on elongated body 12 including hub 14. In some examples, all or a portion of memory 19 may be removable from elongated body 12 and may be located on or adjacent with sensor 20. Data sensed by sensor 20 may be stored on memory 19, e.g., for later retrieval by external device 24 and/or for processing of the sensor information from sensor 20. While memory 19 is shown as being separate from sensor 20, in some examples, sensor 20 may additionally or alternatively include another memory for storing data from sensor 20. In one example, memory 19 may be located on an integrated circuit (IC) with processing circuitry and communication circuitry which may enable memory 19 to communicate with external device 24 wirelessly. Further, the IC may be hermetically sealed to prevent any bodily fluids or other material from damaging memory 19. In another example, memory 19 or a memory IC may be coupled to an IC coupler on elongated body 12.

In some examples, memory 19 may include all or a portion of sensor information received from sensor 20. One or more sensors 20 may be positioned on elongated body 12 and the sensors 20 may sense a parameter of a fluid within the lumen of the elongated body. Sensor information stored on memory 19 may be communicated with external device 24, 28, or 30. Each of external devices 24, 28, or 30 may represent, in some examples, external devices located in certain areas of care. For example, external device 24 may be located in an operating room, external device 28 may be located in an intensive care room and external device 30 may be located in a recovery room. In some examples, medical device 10 may have processing circuitry on elongated body 12 including hub 14 that may control all or some operations of sensor 20. In some examples, the processing circuitry of external device 24 may control all or some operations of sensor 20. In some examples, the processing circuitry of external device 24 and processing circuitry of medical device 10 may control all or some of operations of sensor 20 together. Memory 19 may also receive patient-specific information and device data, such as a time stamp and device identification number, from external device 24, that memory 19 may store onboard after being communicatively disconnected from external device 24 through connection 26 that may be physically wired or wireless. Connection 26 is discussed below, but connection 26 may communicating information between memory 19 and external devices 24, 28, or 30. Further, memory 19 may then share this information with another external device in the event external device 24 breaks down or in the more likely event the patient to whom medical device 10 is inserted into may be moved from surgery to an intensive care. In intensive care, memory 19 may now communicate with another external device and share patient-specific information collected from surgery.

Medical device 10 may be used throughout an entire medical process. For example, medical device 10 may be used to monitor kidney function in many areas of care, such as, a pre-operation room, an operating room, ICU (intensive care unit), and in recovery. Medical device 10 may be used with one patient but may be used in more than one area of care. External device 24, when used in conjunction with medical device 10, will remain in one area of care and not travel with a patient (not shown in FIG. 1). Clinicians in an area of care want to know the history of sensor measurements and patient-specific history as a patient moves from one area of care to another (e.g., from the operating room to the ICU). In examples of the present disclosure, sensor information from sensor 20 may be recorded entirely or partially on memory 19. When the patient is moved from a first area (such as the operating room) to a second area (such as the ICU) and from a first external device to a second external device, the second external device located in the ICU may access the sensor information on memory 19 and display patient-specific historic data on the second external device. Further, the second external device may access prior patient-specific information stored on memory 19 by the first external device while the patient was in the operating room coupled to the first external device. Thus, a clinician in the ICU, utilizing the second external device may see past patient-specific information including sensor information collected on memory 19. This patient-specific information may assist the clinician in determining or otherwise evaluating a patient's condition, e.g., by determining a patient's risk of developing AKI and overall kidney health.

In one example, medical device 10 may be used by a cardiac anesthesiologist in the operating room with a first external device. In the ICU, an intensivist may need to know what occurred in the operating room during surgery and if the patient is at a high or low risk for developing AKI. By recalling the patient-specific information including the sensor information reordered on memory 19 during the surgery, the intensivist, who was not in the operating room, may review intraoperative monitoring data specific to the patient without having to access the patient's electronic health records. In another example, the patient's electronic health records or a portion of the patient's health records may be loaded onto memory 19 by the external device in the operating room during surgery. Once the intensivist couples the second external device to memory 19, they may have access to a patient's sensor information and sensor history, patient-specific information and a patient's electronic health record to better a patient's kidney health and potential for developing AKI.

Memory 19 may allow inputs of events in surgery such as the start and stop of different epochs, drug administrations to the patient, blood transfusions to the patient, aortic cross-clamping times, or other intraoperative events that may have an effect in a patient developing AKI. Each of the epochs may be used by a clinician in another area of care to evaluate a patient's kidney health or the data may be used by an AKI risk algorithm that calculates a patient's probability of developing AKI. Each one of these epochs would also be examples of patient specific information. Memory 19 may also save patient specific information such as inputs like lab results, that may be part of the patient's electronic medical record, such as hematocrit, arterial partial pressure of oxygen, AKI biomarker tests, serum creatinine, or other lab results. These inputs may be loaded into memory 19 manually by a clinician or automatically added from the patient's electronic medical record. Patient-specific information may be any electronic information regarding a patient's health including information stored in medical records, sensor data, inputted epoch information by a clinician and any other electronic data regarding a patient's health that may be stored on memory 19.

In another example, the sensor information which is another type of patient-specific information, may be recorded on memory 19 may be used to calculate a risk of AKI score. For example, external device 24 located in an operating room may use pre-operative patient characteristics, such as sensor information or patient-specific information recorded onto memory 19 by an external device prior to the operating room. The sensor information and patient-specific data may be continuously updated as new information is generated and thus external device 24 may use a real time prediction algorithm to determine and calculate a risk of AKI sore.

External device 24 may be used to calculate the risk of developing AKI based on the sensor information and patient-specific information recorded on memory 19. The risk of developing AKI may be reflected in an AKI risk score. The value may be indicative of the relative risk of developing AKI. The risk score may be numerical or color coded or expressed in another suitable manner. The AKI risk may be summarized in a procedural report and stored on memory 19. The report may include the risk of AKI, an AKI risk score and other information like length or intensity of hypoxia. The summary report may be recorded to memory 19 and later accessed by other external devices or possibly added to the patient's electronic medical record.

External device 24 and other external devices may process an algorithm that calculates, displays and stores on memory 19 a continuously updated and real-time risk of developing AKI. The algorithm may continuously update the AKI risk based upon all information inputted, including all sensor measurements made and patient-specific information stored on memory 19. As a patient is moved from one area of care to another area of care and medical device 10 is coupled to a new external device 24, the algorithm may quickly access the patient-specific information including sensor information on memory 19 and begin to calculate a real-time risk of AKI. The patient-specific data may also include sensor information collected during the patient's move from area of care to another when no external device is coupled to memory 19. The patient-specific information may be presented to the clinician showing: (1) each of a measure parameter of a fluid within lumen 34, such as urine flow rate, amount of dissolved oxygen in the urine, etc., (2) a calculated estimate of renal function or perfusion, and (3) a predicted risk of developing AKI including an AKI risk score. Further, all this information may be stored back upon memory 19 for the patient to take with them as long as they have medical device 10 associated with the patient. In another example, this patient-specific information may be stored as real-time spot measurements (e.g., for a moment in time look), a time average value, and/or trends from baseline values (e.g., the patient's values in pre-operation or known healthy baselines for the patient). This information may be displayed at external device 24 along with alarms (e.g., audible, visual or tactile) when threshold values are exceeded.

Memory 19 may store program instructions, such as software or algorithms, including an AKI risk prediction algorithm, that may include one or more program modules, that are executable by processing circuitry (not shown in FIG. 1). When executed by the processing circuitry, such program instructions may cause the processing circuitry and external device 24 to provide the functionality ascribed to them herein. The program instructions may be embodied in software and/or firmware. Memory 19 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

In accordance with examples of the disclosure, medical device 10 may include one or more sensors that may be configured to monitor one or more parameters of a fluid within lumen 34 (FIG. 2) of elongate body 12. For example, in FIG. 1, medical device 10 includes sensor 20. Sensor 20 may be configured to sense one or more of a temperature, flow rate, light, fluorescence, oxygen, sound, flow velocity, density or specific gravity of a fluid in elongate body 12, e.g., of a fluid within lumen 34 of elongate body 12.

In an example of the present disclosure sensor 20 may be configured to sense the flow rate of urine or other fluid within elongate body 12. For example, as described further below, sensor 20 may be a thermal dilution sensor. Additionally, or alternatively, sensor 20 may be configured to monitor or otherwise determine the flow of a fluid within elongated body 12 using ultrasonic techniques. Additionally, or alternatively, sensor 20 may be configured to sense or otherwise monitor the composition of a fluid (e.g., the amount or concentration of oxygen within the fluid) within elongated body 12 using a fluorescence lifetime technique. In another example of the present disclosure, sensor 20 may be configured to sense at least one flow parameter of a fluid within lumen 34 of elongated body 12 to allow for medical device 10 or other device to determine (e.g., via processing circuitry) at least one of a density parameter or a temperature parameter of the fluid in lumen 34 based on the sensed flow parameter of the fluid.

In some examples, sensor 20 may be representative of a single sensor or multiple sensors. Where sensor 20 may be multiple sensors, the multiple sensors may be located on the elongated body at the same location or at different locations despite being shown at a single location in FIG. 1. Sensor 20 may communicate sensor information to memory 19 and memory 19 to external device 24 via an electrical, optical, wireless or other connection. In some examples, sensor 20 may communicate sensor information to memory 19 through connection(s) within elongated body 12 of medical device 10 from proximal portion 17B to distal portion 17A via embedded wire(s) or optical cable(s). In other examples, sensor 20 may communicate sensor information to memory 19 via a wireless communication technique.

Sensor 20 may be positioned on distal portion 17A of elongated body 12 of medical device 10 including portions of elongated body 12 positioned distal to distal end 12A connected to a fluid collection container (e.g., a urine bag) or the like. Sensor 20 may be an oxygen sensor utilizing a florescence lifetime technique.

In some examples, sensor 20 is mechanically connected to elongated body 12 or another part of medical device 10 using any suitable technique, such as, but not limited to, an adhesive, welding, by being embedded in elongated body 12, via a crimping band or another suitable attachment mechanism or combination of attachment mechanisms. Sensor 20 may be removably coupled to elongated body 12. That is, sensor 20 may be coupled to elongated body 12 and used for a procedure and then sensor 20 may be removed, coupled to another elongated body and used again. In some examples, elongated body 12 includes a structure distal to a distal end of medical device 10, such as tubing extending between hub 14 and a fluid collection container, that sensor 20 may be coupled to.

In some examples, sensor 20 may be disposable and/or reusable. In some examples, sensor 20 may be disposed of, such as placed into medical waste, when elongated body 12 is through being used for a medical procedure. In some examples, all or a portion of sensor 20 may be reusable and detachable from elongated body 12 so sensor 20, or a portion thereof, may be used again on another elongated body for the same, similar or different procedure. For purposes of the disclosure disposable may be defined as an article intended to be used once, or until no longer useful, and then thrown away. Reusable may be defined as an item that may be used again or more than once. A reusable sensor may be configured such that sensor may be coupled to elongate body 12 so that it functions as described in the examples of the disclosure, subsequently removed from elongate body 12 and then coupled to another elongate body in a manner that allows the sensor to again function as described herein on the another elongated body.

Sensor 20 may be configured to communicate sensor information to memory 19. External device 24 may be a computing device, such as a workstation, a desktop computer, a laptop computer, a smart phone, a tablet, a server or any other type of computing device configured to receive, process and/or display sensor information including patient-specific information stored on memory 19, AKI risk score data, or AKI predictive algorithm data. Sensor 20 may communicate sensor information to the memory 19 and to external device 24 via a connection 26. Connection 26 may be an electrical, optical, wireless or other connection.

Elongated body 12 may be structurally configured to be relatively flexible, pushable, and relatively kink- and buckle-resistant, so it may resist buckling when a pushing force is applied to a relatively distal portion of medical device 10 to advance elongated body 12 proximally through the urethra and into the bladder. Kinking and/or buckling of elongated body 12 may hinder a clinician's efforts to push the elongated body proximally. Any suitable material may be used for elongated body 12, such as a suitable biocompatible polymer or other biocompatible material.

Figure 2:
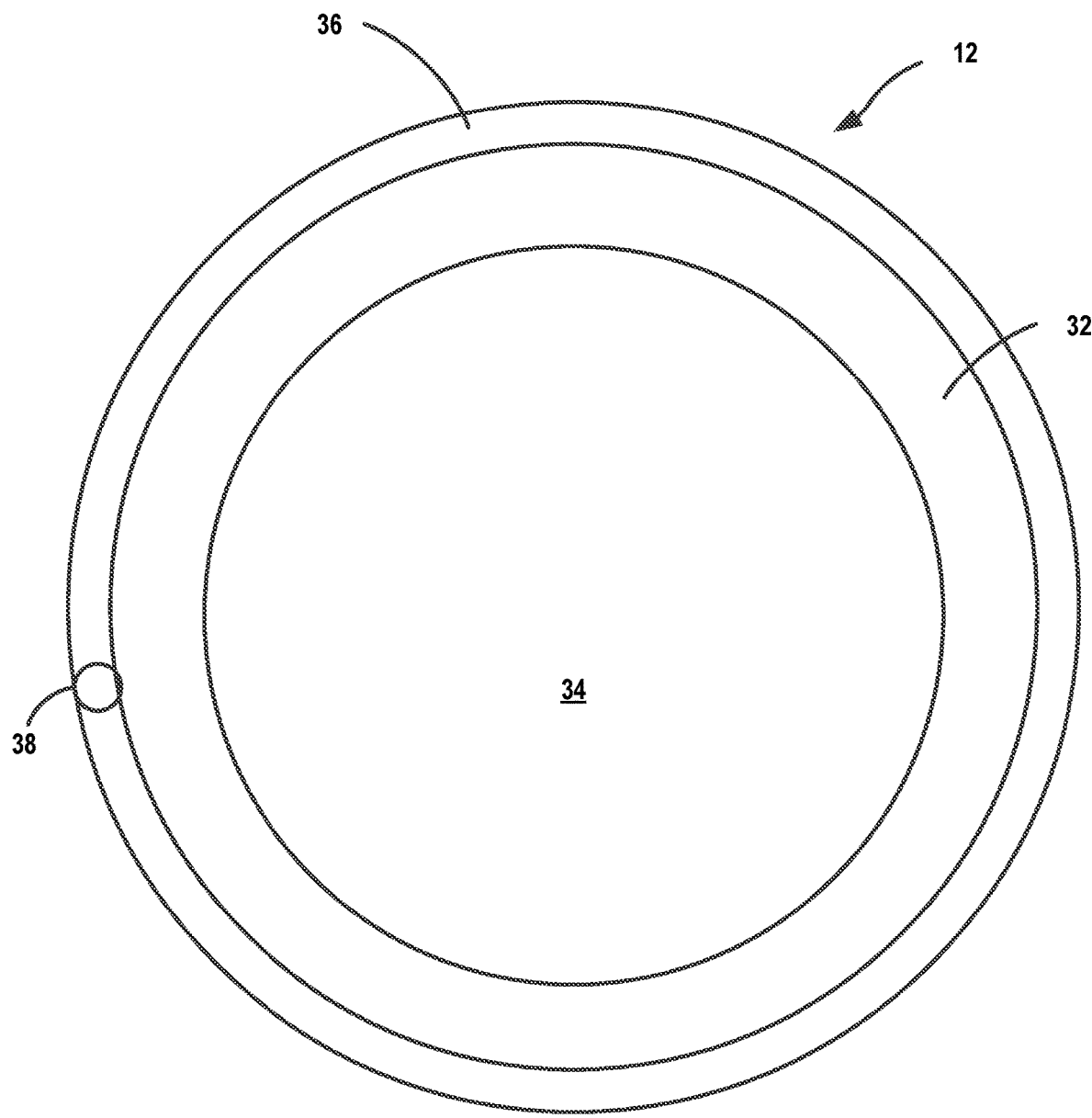
FIG. 2 is a diagram illustrating example a cross-section of the medical device of FIG. 1, the cross-section being take along lines 2-2 of FIG. 1.

FIG. 2 is a diagram illustrating an example cross-section of medical device 10, where the cross-section is taken along line 1-1 in FIG. 1 in a direction orthogonal to central longitudinal axis 16. FIG. 2 depicts a cross section of elongated body 12, that defines lumen 34 and lumen 36. In some examples, lumen 34 may be referred to as a drainage lumen, such as in examples in which medical device 10 is a Foley catheter configured to drain urine from a bladder of a patient, and lumen 36 may be referred to as an inflation lumen in examples in which lumen 36 is configured to deliver an inflation fluid to anchoring member 18. Elongated body 12 may enclose connection 38.

Lumen 34 may serve as a passage for urine entering medical device 10 through fluid opening 13 to fluid opening 14A. In the example shown in FIG. 2, lumen wall 32 is relatively non-permeable to substances of interest, such as oxygen and/or carbon dioxide, and positioned between lumen 36 and lumen 34. In some examples, lumen wall 32 extends along an entire length of lumen 34, while in other examples, lumen wall 32 only extends along only a part of a length of lumen 34, for example, from a portion of lumen 34 intended to be in a patient's bladder during use, that may help maintain a desired level of flexibility of elongated body 12. In addition, as shown in FIG. 2, in some examples, lumen wall 32 extends around an entire outer perimeter of lumen 34 (e.g., an outer circumference in examples in that the inner perimeter is circular in cross-section).

Inflation lumen 36 may serve as a passage for a fluid, such as sterile water or saline, or a gas, such as air, from inflation opening 14B to anchoring mechanism 18. For example, an inflation device (not shown) may pump fluid or gas into inflation lumen 36 through inflation opening 14B into anchoring member 18 so anchoring member 18 is inflated to a size suitable to anchor medical device 10 to the patient's bladder. While inflation lumen 36 is shown as circular in cross section, it may be of any shape. In some examples, there may be a plurality of inflation lumens. For example, a plurality of inflation lumens may substantially surround lumen 34. In some examples, anchoring member 18 may be an expandable structure not an inflatable balloon. In such examples, inflation lumen 36 may be replaced by a deployment mechanism that may permit a clinician to expand the expandable structure. For example, inflation lumen may be replaced by a mechanical device pushed and pulled separately from the medical device 10 by a clinician to expand or retract the expandable structure.

Connection 38 may serve to connect sensor 20 positioned at distal portion 17A to memory 19. Connection 38 may be an electrical, optical or other connection. In some examples, connection 38 may comprise a plurality of connections. For example, connection 38 may include one of more wired or optical connections to a temperature sensor and one or more connections to a pressure sensor. In some examples, connection 38 may include one or more power connections to power sensor 20 and one or more communications connections to receive sensor information from sensor 20.

Figure 3:
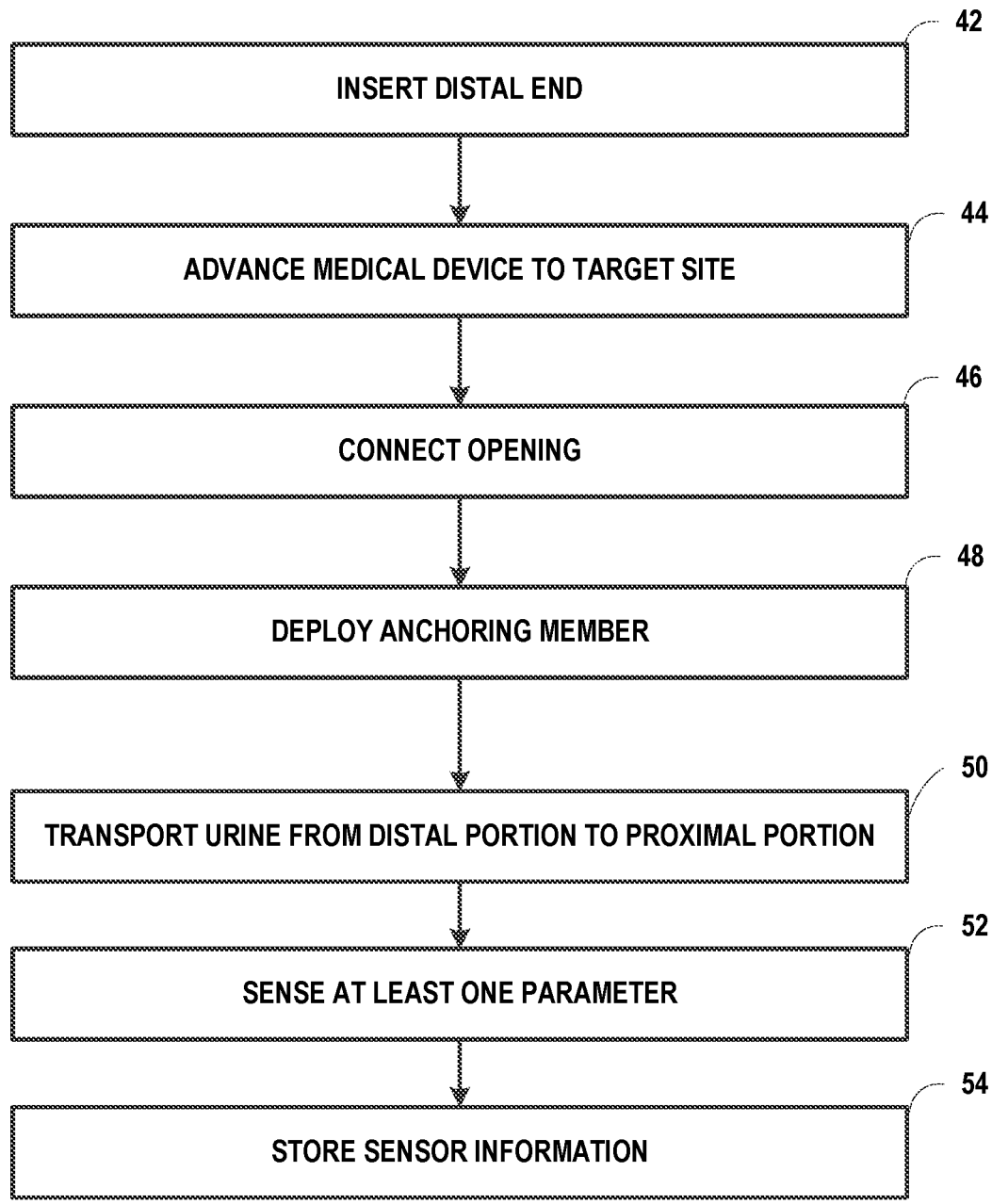
FIG. 3 is a flow diagram illustrating an example method of operating a medical device according to the techniques of this disclosure.

FIG. 3 is a flowchart illustrating an example operation of medical device 10. A clinician may insert proximal end 12B of medical device 10 into a patient's urethra (42). The clinician may advance medical device 10 through the patient to a target site (44), e.g., until uninflated or undeployed anchoring member 18 is within the patient's bladder (44). The clinician may connect inflation opening 14B to an inflation device and may connect fluid opening 14A to a fluid collection container and/or to external sensors (46). The clinician may then deploy anchoring member 18 to help secure medical device 10 relative to the target site (48). For example, the clinician may inflate anchoring member 18, for example, using an inflation device and inflation fluid, such as sterile water, saline, or a gas. In examples in that anchoring member 18 is an expandable structure, the clinician may deploy anchoring member 18 by pushing a structure radially outwards or pulling back on a structure to cause the expandable structure to expand radially outwards.

Lumen 34 may transport urine from the proximal portion 17B of medical device 10 to the distal portion 17A of medical device 10 (50). Sensor 20 may sense at least one parameter, such as temperature and/or oxygen, from urine being transported through lumen 34 (52). For example, sensor 20 may sense a parameter such as urine flow (e.g., fluid velocity or volume), and/or amount of dissolved oxygen in the urine. In some examples, sensor 20 may sense at least one parameter between medical device 10 and a fluid collection container, e.g., at the distal end of elongate body 12. The sensor information sensed by sensor 20, along with other patient-specific information, may be stored on memory 19 (54).

While the example of FIG. 3, sets forth a number of steps, these steps may be performed in a different order or concurrently. For example, the clinician may connect the inflation opening 14B to an inflation device and/or may connect fluid opening 14A to a fluid collection container and/or to sensor 20 prior to inserting the proximal end 12B of medical device 10 into the patient's urethra and lumen 34 may transport urine concurrently with sensor 20 sensing any parameters.

Figure 4:
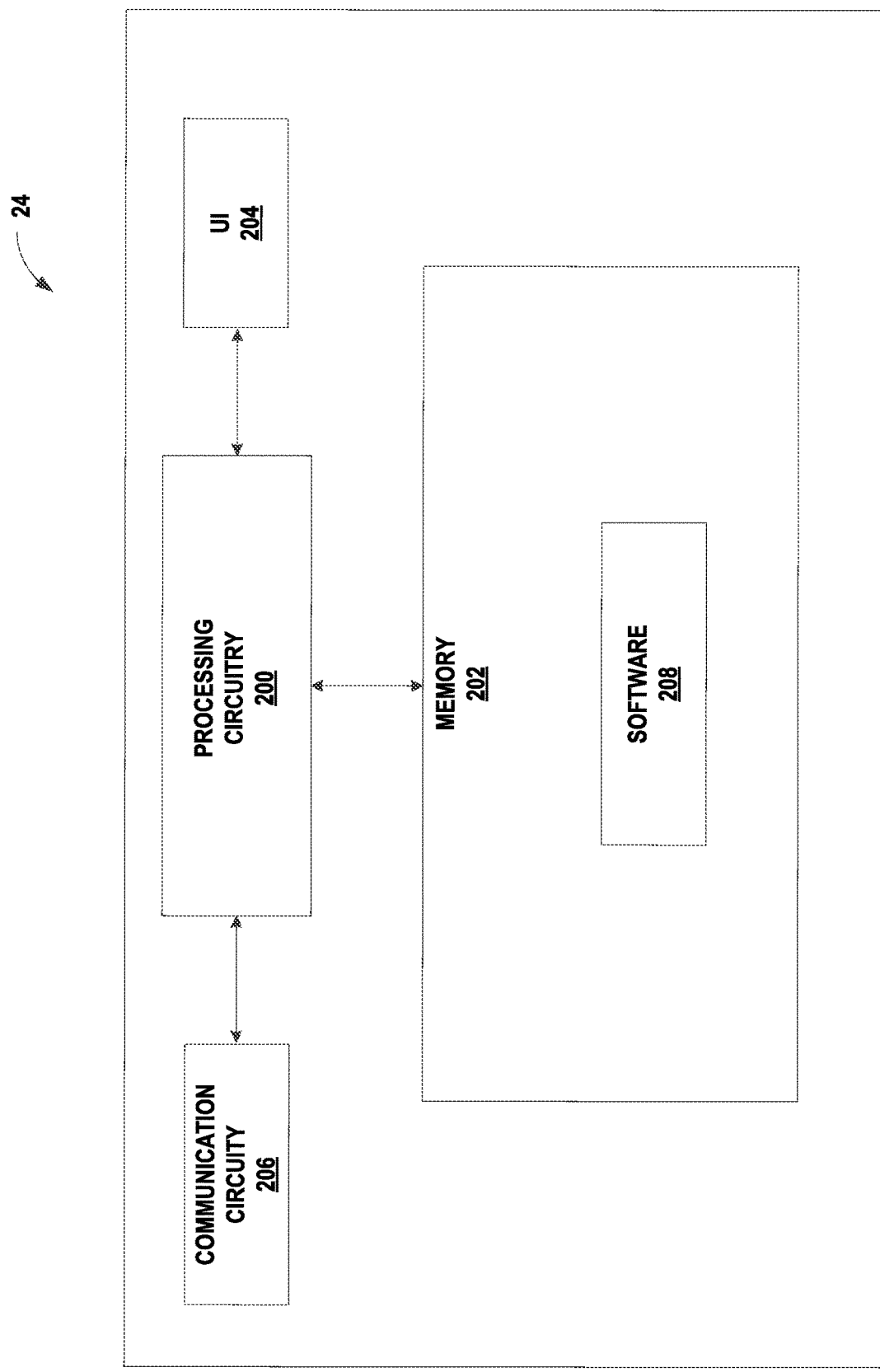
FIG. 4 is a block diagram of an example external device used with a medical device according to the techniques of this disclosure.

FIG. 4 is a functional block diagram illustrating an example of an external device 24 configured to communicate with sensor 20, receive information from sensor 20 and store and retrieve information from memory 19. In the example of FIG. 4, external device 24 includes processing circuitry 200, memory 202, user interface (UI) 204, and communication circuitry 206. External device 24 may be a dedicated hardware device with dedicated software for reading sensor information. Alternatively, external device 24 may be an off-the-shelf computing device, e.g., a desktop computer, a laptop computer, a tablet, or a smartphone running a mobile application enabling external device 24 to read sensor information from sensor 20 and memory 19.

In some examples, a user of external device 24 may be clinician, physician, intensivist, or healthcare giver. In some examples, a user uses external device 24 to monitor a patient's kidney function, e.g., based on information sensed by sensor 20 or otherwise derived from information sensed by sensor 20 in the manner described herein. In some examples, the user may interact with external device 24 via UI 204, that may include a display to present a graphical user interface to the user, and a keypad or another mechanism (such as a touch sensitive screen) for receiving input from the user. External device 24 may communicate with sensor 20, memory 19 and/or any other electronic component of catheter 10 using wired, wireless or optical methods through communication circuitry 206.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, such as software 208, that may include one or more program modules, that are executable by processing circuitry 200. When executed by processing circuitry 200, such program instructions may cause processing circuitry 200 and external device 24 to provide the functionality ascribed to them herein. The program instructions may be embodied in software and/or firmware. Memory 202 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Figure 5:
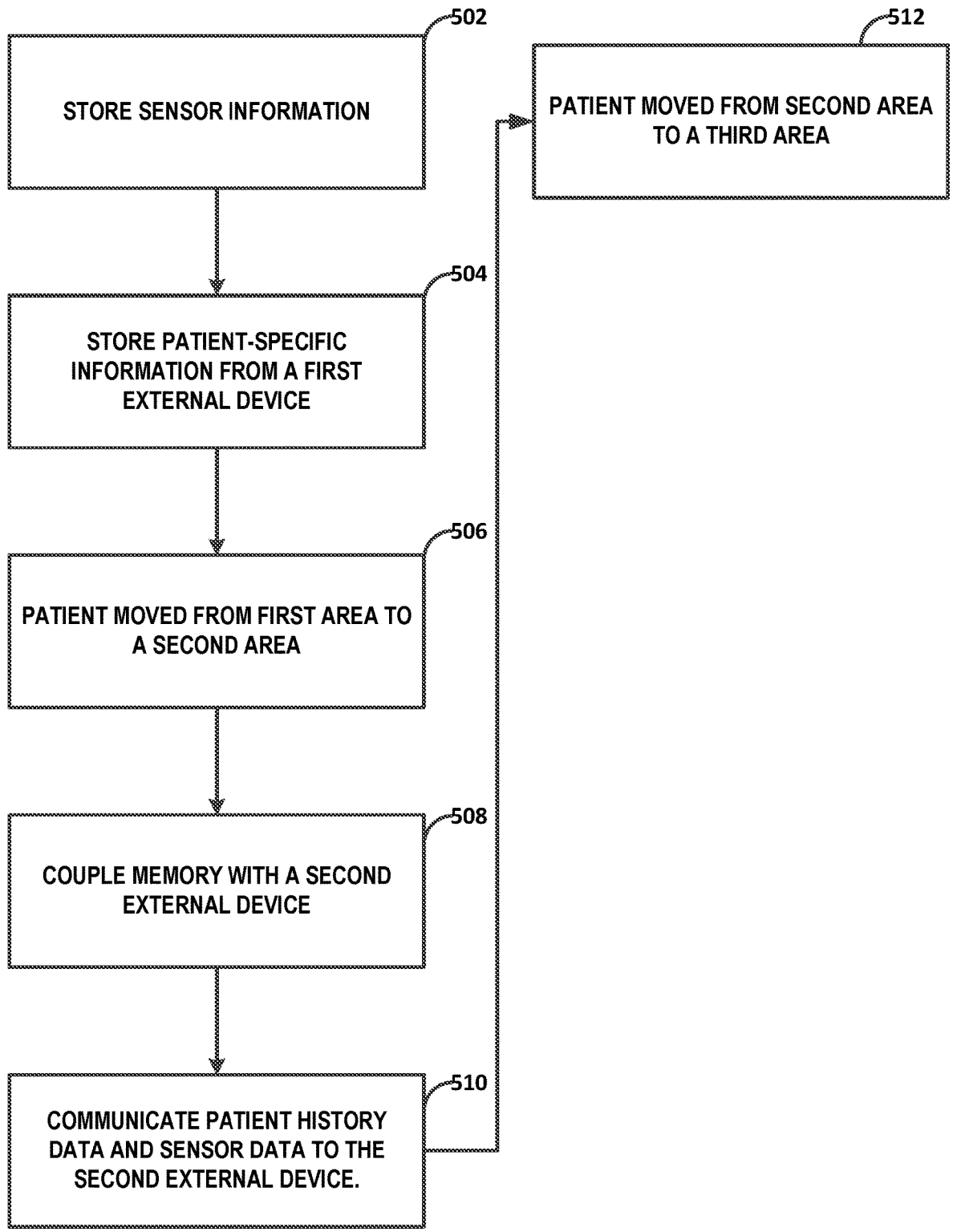
FIG. 5 is a flow diagram illustrating an example technique for recording patient-specific information including sensor information to a memory onboard a catheter according to the techniques of this disclosure.

FIG. 5 is a flow diagram illustrating an example technique for recording patient-specific information including sensor information to a memory onboard a catheter according to the techniques of this disclosure. When medical device 10 has been anchored to a patient, for example as detailed in FIG. 3, sensor 20 may begin to send sensor information to memory 19 after initializing the sensing of a parameter(s) (52, FIG. 3). Sensor information may be sent to memory 19 through connection 38 as it is collected by sensor(s) as described above. In other examples, sensor information may also be sent to memory 19 wirelessly. Memory 19 may then store the sensor information in memory 19 (502). Sensor information may also be considered patient-specific information as it is information specific to a patient. In some examples of the description, sensor information is information emanating directly from one or more sensors 20 onboard or coupled to elongated body 12. Sensor data collected by an external device and stored on memory 19 may be referred to as patient-specific information.

The sensor information may come from one or more sensors 20 detecting one or more parameters of a fluid within lumen 34. These parameters may include, but are not restricted to, fluid flow, fluid velocity, fluid rate, oxygen content, temperature, density, specific gravity, color, acidity, glucose, ketones, nitrates, clarity/turbidity, acidity, blood, and protein. Each parameter sensed by each sensor on elongated body 12 may be stored on memory 19 including each sensor's history of parameters sensed. The sensed history may be stored on memory 19 in whole or in part depending on the storage capacity of memory 19. In some examples, memory 19 may be memory to store all the sensor information collected including sensor history. In some examples, when sensor information is saved to an external device, memory 19 may write over sensor information starting with the oldest sensor information first. In another example, memory 19 may have a storage capacity to store sensor information from each sensor 20 on elongated body 12, including all sensor history as well as patient-specific information stored from an external device throughout the entire use of memory 19.

The sensor information storage process may be performed while elongated body 12 is anchored to the patient and the patient and memory 19 move from one area of care to another or one external device to another. In some examples, memory 19 is large enough to store sensor information and patient-specific information for the entire duration of patient use (e.g., 10-20 gigabytes). In some examples, sensor information and patient-specific information may be encrypted to protect information classified under the health insurance portability and accountability act (HIPAA). Encryption may be desired as elongated body 12 and memory 19 may be disposable. In another example, memory 19 may be removed from elongated body 12, cleared and reused or disposed in a manner consistent with the safeguards detailed in HIPAA.

In one example, medical device 10 with elongated body 12 and sensor(s) 20 may be used to monitor kidney function of a patient in an operating room during a medical procedure. Memory 19 may be coupled to external device 24 wirelessly or through connection 26 (FIG. 1). Once memory 19 is coupled to external device 24, external device 24 may store any patient-specific information contained on or inputted into memory 202 (FIG. 4) onto memory 19 (504). This process may be performed by prompting the clinician at user interface 204 (FIG. 4) to share patient-specific information with memory 19. In another example, the sharing of patient-specific information onboard memory 200 may be automatic upon coupling memory 19 to external device 24. Further, the sharing of patient-specific information may be continuous or intermittent (e.g., transferred every 10 seconds). Examples of patient-specific information may include patient age, sex, medical history, type of surgery (e.g., elective or emergency), co-morbidities, etc.

After the patient's surgical procedure is completed the patient may be moved to recovery in an ICU (506). One elongated body 12 may be used with one patient, but elongated body 12 may be used in more than one area of care. However, external device 24 used during the surgical process stays in the surgical area of care and does not travel with the patient. Nevertheless, the patient-specific information, including sensor information from sensor(s) 20, used by clinicians in sugary may be transferred with memory 19. An intensivist in the ICU may want to know the history of the patient while in the surgical room when the catheter was used with a different external device.

The sensor information and patient-specific information may be recorded completely or partially on memory 19 such that when an external device is connected to a new external device (508) the new external device may download and display historic patient-specific information from the prior external device or devices and in doing so allow the clinician to see past patient-specific information for a patient (510).

For example, in the intensive care unit (ICU), the intensivist may want to know what occurred in surgery and if the patient is at high or low risk for developing AKI. By recalling the patient-specific information through user interface 204 (FIG. 4) recorded on memory 19 during surgery, the intensivist who was not in the operating room may review intraoperative monitoring information without having to access electronic health records.

Memory 19 may also store clinician inputted events in surgery such as: the start and stop of different epochs (e.g., start of surgery, end of surgery, administration of anesthesia, start and stop of cardiopulmonary bypass, start of rewarming phase), drug administrations to the patient, blood transfusions for the patient, aortic cross-clamping times (e.g., indicating times when low blood flow may be expected), or other intraoperative events. The different epochs may, for example the rewarming phase, be impactful to the health of the patient's kidneys. Each epoch may have a different impact in determining potential AKI risk. Memory 19 may also record external device inputs like lab results such as hematocrit, arterial partial pressure of oxygen, AKI biomarker tests, serum creatinine, or other lab results. The inputs may be manually completed by the clinician or be automatically added from the electronic medical record. Further, any sensor not coupled to or part of elongated body may have its information stored on memory 19 as well. In an example, electrocardiogram (ECG), blood pressure, heart rate, pulse oximetry, respiration as well as many other patient-specific parameters that may be monitored during a surgical process. This information may be downloaded to memory 19 through an external device or directly through electronic medical records.

In another example, the patient may be moved from the ICU to a recovery room or another transition room (512). Memory 19 may, again, communicate with an external device in the recovery area of care. The external device in the recovery room may quickly download the patient-specific data from memory 19, present this information to a clinician or intensivist, process any possible alarms and present an AKI risk report along with an AKI risk score. The patient-specific information recorded by memory 19 during surgery may be used to calculate a risk of AKI score that may be based on pre-operative patient characteristics and continuously updated as new information or data is generated.

Figure 6:
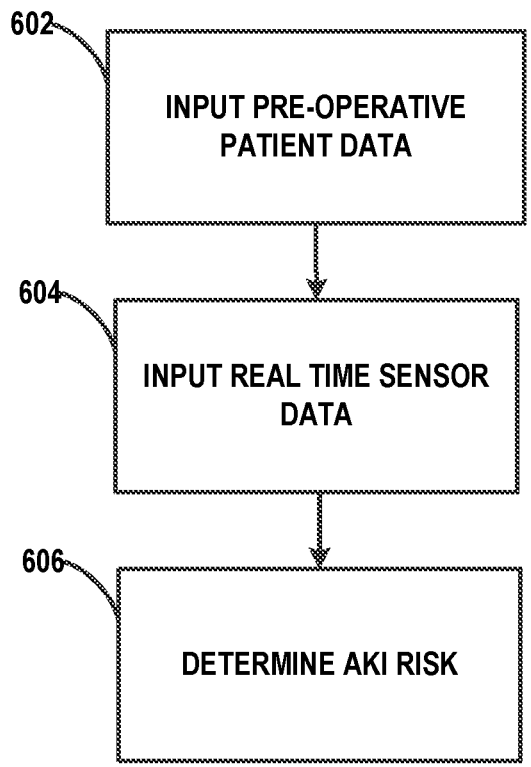
FIG. 6 is a flow diagram illustrating an example technique for determining real-time AKI risk assessment according to techniques of this disclosure.

FIG. 6 is a flow diagram illustrating an example technique for determining real-time AKI risk assessment according to techniques of this disclosure. In examples of the disclosure, an AKI risk assessment algorithm may provide a continuously updated real-time AKI assessment. In other examples, the AKI risk assessment algorithm may provide a substantially instantaneous AKI assessment of a patient when they are moved from one area of care to another area of care. The AKI risk assessment algorithm may continuously store a real-time report of the patient's risk in developing AKI. This real-time AKI report may be continuously transferred to memory 19 and travel with the patient as they move from one area of care to another. The report may then be quickly accessed by an external device in the new area of care and an AKI risk assessment may be quickly determined and provided to a clinician or intensivist in charge of monitoring the patient. In some examples, the real-time risk assessment may be continuously updated as the patient moves from one area of care to another. For example, the AKI risk assessment algorithm may be stored on memory 19 and be executed by processing circuitry on elongated body 12. In another example, a second AKI risk assessment algorithm may be stored on memory 19 and as a patient is moved from one area of care to another area of care, processing circuitry onboard elongated body 12 may process inputs from sensor 20 to continuously update an AKI risk assessment. Then, upon the patient reaching the next area of care, an updated AKI risk assessment may be accessed by an external device and a clinician informed of the patient's AKI status.

In examples of the present disclosure, external device 24 may have an AKI risk assessment algorithm. The AKI risk assessment algorithm may be located within software 208 (FIG. 4) located in memory 202. In other examples, the AKI risk assessment algorithm may be stored onboard memory 19. In yet another example, the AKI risk assessment algorithm may be located in both memory 202 and memory 19. External device 24, using processing circuitry 200, may process the AKI risk assessment algorithm when memory 19 is coupled to the external device. When memory 19 is not coupled to an external device, the AKI risk assessment algorithm stored on memory 19 may be processed by processing circuitry onboard elongated body 12. In this fashion, the AKI risk assessment algorithm may be consciously update and the most accurate assessment may be provided to the clinician or the intensivist.

The AKI risk algorithm may rely on pre-operative patient-specific information, such as patient demographics (e.g., date of birth, gender, blood type, ethnicity, etc.), co-morbidities (e.g., hypertension, fluid and electrolyte disorder, chronic pulmonary disease, deficiency anemias, etc.), and other physiologic characteristics (e.g., composition of plasma, specific gravity, plasma proteins, free serum amino acids, blood volume, blood pressure and heart rate, blood PH, oxygen consumption, respiratory rate, basal metabolism, etc.) that may be inputted manually by a clinician or automatically by electronic medical records before a surgical procedure (602). The preoperative information may also include any sensor information (e.g., temperature, flow rate, light, fluorescence, oxygen, sound, flow velocity, density or specific gravity) from one or more sensor 20 located on elongated body 12.

The AKI risk assessment algorithm may be continuously updated with information from memory 19. Further, memory 19 is continuously updated with information from external device 24, including an updated AKI risk assessment report. As discussed above, external device 24 has access to memory 19 and is continuously getting input from sensor 20 on elongated body 12. The AKI risk assessment algorithm may calculate and display a continuously updated and real-time risk of developing AKI based upon the continuously updated sensor information from memory 19 and patient-specific information in memory 202 or memory 19.

The AKI risk assessment algorithm may be an existing pre-operative AKI risk algorithm. The AKI risk assessment algorithm may be modified so that it continuously accepts updated sensor information from sensor 20 and patient-specific information through external device 24 determined before, during and after a surgical process (604). Patient-specific information may include cardiac output, blood pressure, pulse oximetry, hematocrit, arterial partial pressure of oxygen, AKI biomarker tests, serum creatinine, other lab results or any information that may have an affect on AKI developing. Further patient-specific information may include events in surgery such as the start and stop of different epochs, drug administrations, blood transfusions, aortic cross-clamping times, other intraoperative events or any events that may have an affect on AKI developing.

The AKI risk assessment algorithm may present this information in the form of a report or display on user interface 204 (FIG. 4). The AKI risk assessment algorithm may display sensor information from one or more of sensor 20, such as urine flow rate, amount of dissolved oxygen in urine, etc. The AKI risk assessment algorithm may display a calculated estimate of renal function or perfusion. The AKI risk assessment algorithm may also display a predicted risk of developing AKI (606). The AKI risk assessment may be done based on patient-specific or operation specific data. The AKI risk assessment algorithm may incorporate many more variables, such as urine oxygenation and urine output, in providing an AKI risk assessment that incorporates more patient-specific information to obtain the AKI risk assessment. The AKI risk assessment algorithm may also initiate an alarm to indicate an upper or lower threshold has been surpassed and an AKI risk is growing or great. This AKI risk assessment alarm may be audible, visual or tactile or a combination of one or more of these types of alarms.

All of the information provided by the AKI risk assessment algorithm may be in the form of real-time spot measurements, time average values, and/or trends from baseline values. The information may be numeric or graphic. Alarms may be implemented and programmed to alert the clinician when threshold values are exceeded. The AKI risk assessment algorithm is continuously saving an updated AKI risk assessment to memory 19. Thus, whenever the patient is moved from one area of care to another area of care, the next clinician or intensivist responsible for the patient may quickly know a patient's risk of developing AKI as soon as memory 19 is coupled with an external device in the new area of care.

Figure 7:
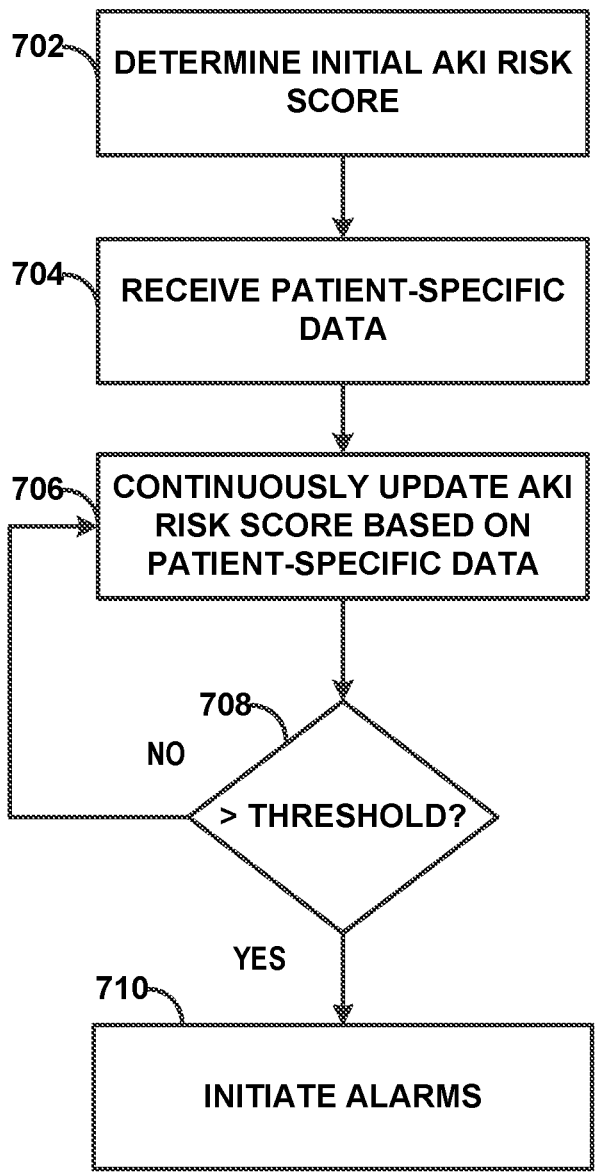
FIG. 7 is a flow diagram illustrating an example technique for determining an AKI risk score and summary report according to techniques of this disclosure.

FIG. 7 is a flow diagram illustrating an example technique for determining an AKI risk score and summary report according to techniques of this disclosure. The AKI risk assessment algorithm may, as part of its functionality, provide an AKI risk score which may provide a clinician or intensivist with an understanding of a patient's risk of developing AKI. Several factors may be involved with determining the initial AKI risk score (702) (e.g., too little urine being detected at sensor 20, retention of water, respiratory issues, seizures, blood loss, etc.). Processing circuitry 200 may initially determine an AKI risk score for a patient, e.g., prior to anesthetization. While the patient is under anesthesia, processing circuitry 200 may then receive input signals, e.g., from sensors 20 indicative of one or more physiological parameters of patient 202 (704).

The AKI risk assessment algorithm may be continuously updated with patient-specific data, including sensors coupled to the external device, clinician inputs and the patient's electronic medical records to calculate the risk of developing AKI (706). The AKI risk score may be summarized in a procedural report including the risk and other information like length or intensity of hypoxia. The summary report may be recorded to the memory 19, pulled up on external devices, or added to the electronic medical record. Based on patient-specific information, processing circuitry 200 may generate an updated AKI risk score. Processing circuitry 200 may then determine whether or not the determined AKI risk score is below a predetermined threshold (708), e.g., stored in memory 19 or memory 202. If the determined AKI risk score is below the threshold, then processing circuitry 200 returns to state 706 to continuously update the AKI risk score ("NO" arrow of block of 708). Additionally or alternatively, if the determined AKI risk score is above the threshold, then processing circuitry 200 may present (e.g., via user interface 204, via an auditory alert, via a haptic alert, or any combination thereof) a notification to the clinician that indicate a high risk for the patient developing AKI ("YES" arrow of block 708) (710). In one example, the AKI risk score may be implemented in a percentage basis of developing AKI. For example, a 0% AKI risk score may mean the patient has almost no chance of developing AKI, while a score of 75% may mean the patient has a very real chance of developing AKI and preventative measures need to be taken. In another example, based on pre-operative data a patient may have a 15% chance of developing AKI and based on poor urine oxygenation during surgery, this percentage may increase to 45% and thus the score would indicate to a clinician the patient may need steps taken to abate AKI.

An AKI risk score may be presented to a clinician as a stage (e.g., stage 1, stage 2 or stage 3) or at rating scale such as a number out of 10 (e.g., 5 out of 10). The AKI risk score may also be linked to an alarm system providing audible, visual, or tactile indications of an alarm.

The AKI risk score may be continuously calculated and recorded onto memory 19. When a patient was moved from one area of care to another area of care the AKI risk score may be quickly know by coupling memory 19 to another external device in the new area of care. In another example, the AKI risk score may be updated as the patient is moved from one area of care to another. Processing circuitry on elongated body 12 may process an AKI risk assessment algorithm on memory 19. Thus, a patient may arrive at a new area of care with an updated in real time AKI risk score to present to the next area of care clinician or intensivist. In another example, sensor information is continuously stored on memory 19 while a patient is moved from one area of care to another. When the patient reaches their new area of care, the most recent sensor information is processed by the external device and an AKI risk score is calculated and displayed or shown to the clinician or intensivist.

An AKI risk score allows a clinician or intensivist to quickly assess a patient's kidney status without examining a lot of information. The clinician is allowed to make a quick determination of patient and kidney health. At a later time, the clinician or intensivist may then go through the stored data from memory 19 and assess the patient-specific information and sensor information history.

The following is a non-limiting list of examples that are in accordance with one or more techniques of this disclosure.

Example 1A. A catheter system comprising: an elongated body defining a lumen, the elongated body comprising a proximal portion and a distal portion; an anchoring member positioned on the proximal portion of the elongated body, the anchoring member configured to anchor the proximal portion of the elongated body to a patient; one or more sensors positioned on the elongated body, the one or more sensors configured to sense a parameter of a fluid within the lumen of the elongated body; and memory positioned on the elongated body, the memory configured to store patient-specific information.

Example 2A. The system of example 1A, wherein the patient-specific information includes sensor information collected by the one or more sensors.

Example 3A. The system of any one of examples 1A-2A, wherein at least a portion of the patient-specific information is communicated from an external device via a connection and stored on the memory.

Example 4A. The system of any one of examples 1A-3A, wherein the at least the portion of the patient-specific information stored includes one or more of external device sensor information, pre-operative characteristics for the patient, lab results for the patient, or preoperative events for the patient.

Example 5A. The system of any one of examples 1A-3A, wherein sensor information stored on the memory is communicated to the external device via the connection.

Example 6A. The system of any one of examples 1A-3A, wherein the external device includes a first external device and the at least the portion of the patient-specific information includes a first portion of patient-specific information, the memory configured to communicate the patient-specific information, including the first portion of patient-specific information and the sensor information, with a second external device.

Example 7A. The system of example 6A, wherein the memory is configured to store at least a second portion of patient-specific information from the second external device.

Example 8A. The system of example 7A, wherein the second portion of patient-specific information stored from the second external device includes one or more of second external device sensor information, intraoperative characteristics for the patient, lab results for the patient, or intraoperative events for the patient.

Example 9A. The system of any one of examples 6A-8A, wherein the memory is configured to store an acute kidney injury (AKI) risk score from the first external device, where the first external device generates the AKI risk score based, at least in part, upon the patient-specific information stored on the memory.

Example 10A. The system of any one of examples 6A-9A, wherein the memory is configured to store results from a real-time predictive AKI algorithm communicated from the second external device.

Example 11A. The system of any one of examples 6A-10A, wherein the memory is configured to communicate the patient-specific information, including the first portion and the second portion of the patient-specific information and the sensor information via the connection with a third external device.

Example 12A. The system of example 11A, wherein a third portion of patient-specific information stored by the memory is communicated from the third external device and includes one or more of third external device sensor information, postoperative characteristics for the patient, lab results for the patient, or postoperative events for the patient.

Example 1B. A method comprising: sensing, with one or more sensors positioned on a distal portion of an elongated body anchored to a patient with an anchoring member positioned on a proximal portion of the elongated body, a parameter of a fluid within a lumen defined by the elongated body; and storing, with a memory positioned on the distal portion of the elongated body, patient-specific information that includes sensor information collected by the at least one sensor.

Example 2B. The method of example 1B, wherein the patient-specific information includes sensor information collected by the one or more sensors.

Example 3B. The method of any one of examples 1B-2B, further comprising communicating, at least a portion, of the patient-specific information from an external device via a connection and stored on the memory.

Example 4B. The method of example 3B, wherein the at least the portion of the patient-specific information stored includes one or more of external device sensor information, pre-operative characteristics for the patient, lab results for the patient, or preoperative events for the patient.

Example 5B. The method of any one of examples 3B-4B, further comprising communicating sensor information stored on the memory to the external device via the connection.

Example 6B. The method of any of examples 3B-5B, wherein the external device includes a first external device and the at least the portion of the patient-specific information includes a first portion of patient-specific information, further comprising communicating the patient-specific information, including the first portion of patient-specific information and the sensor information to a second external device.

Example 7B. The method of example 6B, further comprising storing at least a second portion of patient-specific information from a second external device on the memory.

Example 8B. The method of example 7B, wherein the second portion of patient-specific information stored from the second external device includes one or more of second external device sensor information, intraoperative characteristics for the patient, lab results for the patient, or intraoperative events for the patient.

Example 9B. The method of any of examples 6B-8B, further comprising storing an acute kidney injury (AKI) risk score from the first external device, where the first external device generates the AKI risk score based, at least in part, upon the patient-specific information stored on the memory.

Example 10B. The method of any of examples 6B-9B, further comprising storing results from a real-time predictive AKI algorithm communicated from the second external device.

Example 11B. The method of any of examples 6B-10B, further comprising communicating the patient-specific information, including the first portion and the second portion of the patient-specific information and the sensor information to a third external device.

Example 12B. The method of example 11B, further comprising receiving a third portion of patient-specific information stored from the third external device wherein the patient-specific information includes one or more of third external device sensor information, postoperative characteristics for the patient, lab results for the patient, or postoperative events for the patient.

Example 1C. A catheter system comprising: an elongated body defining a lumen, the elongated body comprising a proximal portion and a distal portion; an anchoring member positioned on the proximal portion of the elongated body, the anchoring member configured to anchor the proximal portion of the elongated body to a patient; one or more sensors positioned on the elongated body, the one or more sensors configured to sense a parameter of a fluid within the lumen of the elongated body; and memory positioned on the distal portion of the elongated body, the memory configured to store patient-specific information, wherein the patient-specific information includes sensor information collected by the one or more sensors and patient-data collected from one or more external devices configured to be coupled to the catheter system.

Example 2C. The system of example 1C, wherein the memory is further configured to store a continuously updated AKI risk score by a first external device coupled to the catheter system and wherein the memory is further configured to communicate the patient-specific information, including the AKI risk score with a second external device when coupled to the catheter system.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements.

What is claimed is:

1. A catheter system comprising:
 a Foley catheter comprising:
  an elongated body defining a lumen configured to drain urine from a bladder of a patient, the elongated body comprising a proximal portion and a distal portion; and
  an anchoring member positioned on the proximal portion of the elongated body, the anchoring member configured to anchor the proximal portion of the elongated body to a patient;
  one or more sensors positioned on the elongated body, the one or more sensors configured to sense a parameter of a fluid within the lumen of the elongated body;
  memory positioned on the elongated body, the memory configured to store patient-specific information, the patient-specific information including sensor information sensed by the one or more sensors; and
  processing circuitry configured to process the sensor information;
  wherein the processing circuitry is further configured to determine an acute kidney injury (AKI) risk score based, at least in part, upon the sensor information.

2. The system of claim 1, wherein the processing circuitry is further configured to receive at least a portion of the patient-specific information from an external device via a connection.

3. The system of claim 2, wherein the at least the portion of the patient-specific information includes one or more of external device sensor information, pre-operative characteristics for the patient, lab results for the patient, or preoperative events for the patient.

4. The system of claim 2, wherein the external device is a first external device and the at least the portion of the patient-specific information includes a first portion of patient-specific information, and wherein the processing circuitry is configured to communicate the patient-specific information, including the first portion of patient-specific information and the sensor information, to a second external device.

5. The system of claim 4, wherein the processing circuitry is further configured to receive at least a second portion of patient-specific information from the second external device and store the at least a second portion of patient-specific information in the memory.

6. The system of claim 5, wherein the second portion of patient-specific information includes one or more of second external device sensor information, intraoperative characteristics for the patient, lab results for the patient, or intraoperative events for the patient.

7. The system of claim 1, wherein the processing circuitry is further configured to communicate the sensor information from the memory to the external device via a connection.

8. The system of claim 1, wherein the processing circuitry is configured to process the sensor information utilizing a real-time predictive acute kidney injury (AKI) algorithm.

9. A method comprising:
 sensing, with one or more sensors positioned on a distal portion of an elongated body of a Foley catheter anchored to a patient with an anchoring member positioned on a proximal portion of the elongated body, a parameter of a fluid within a lumen defined by the elongated body, the elongated body being configured to drain urine from a bladder of a patient;
 storing, with a memory positioned on the distal portion of the elongated body, patient-specific information that includes sensor information collected by the at least one sensor one or more sensors;
 processing, with processing circuitry, the sensor information; and
 determining an acute kidney injury (AKI) risk score based, at least in part, upon the patient-specific information.

10. The method of claim 9, further comprising receiving, with the processing circuitry, at least a portion of the patient-specific information from an external device via a connection.

11. The method of claim 10, wherein the at least the portion of the patient-specific information stored includes one or more of external device sensor information, pre-operative characteristics for the patient, lab results for the patient, or preoperative events for the patient.

12. The method of claim 10, wherein the external device includes a first external device and the at least the portion of the patient-specific information includes a first portion of patient-specific information, the method further comprising communicating the patient-specific information, including the first portion of patient-specific information and the sensor information to a second external device.

13. The method of claim 12, further comprising receiving, with the processing circuitry, at least a second portion of patient-specific information from a second external device and storing the at least a second portion of patient-specific information in the memory.

14. The method of claim 13, wherein the second portion of patient-specific information includes one or more of second external device sensor information, intraoperative characteristics for the patient, lab results for the patient, or intraoperative events for the patient.

15. The method of claim 9, further comprising communicating the sensor information from the memory to the external device via a connection.

16. The method of claim 9, wherein processing the sensor information comprises utilizing a real-time predictive acute kidney injury (AKI) algorithm.

17. A catheter system comprising:
a Foley catheter comprising:
an elongated body defining a lumen configured to drain urine from a bladder of a patient, the elongated body comprising a proximal portion and a distal portion; and
an anchoring member positioned on the proximal portion of the elongated body, the anchoring member configured to anchor the proximal portion of the elongated body to a patient;
one or more sensors positioned on the elongated body, the one or more sensors configured to sense a parameter of a fluid within the lumen of the elongated body;
memory positioned on the elongated body, the memory configured to store patient-specific information, the patient-specific information including sensor information collected by the one or more sensors and patient-data collected from one or more external devices configured to be coupled to the catheter system; and
processing circuitry configured to process the sensor information;
wherein the processing circuitry is further configured to determine an acute kidney injury (AKI) risk score based, at least in part, upon the sensor information.

18. The system of claim 17, wherein the processing circuitry is further configured to determine and continuously update an acute kidney injury (AKI) risk score stored by the memory.

\* \* \* \* \*